(12) United States Patent
Iwasaka

(10) Patent No.: US 10,456,020 B2
(45) Date of Patent: Oct. 29, 2019

(54) ENDOSCOPIC SURGERY DEVICE

(71) Applicant: FUJIFILM Corporation, Tokyo (JP)

(72) Inventor: Masayuki Iwasaka, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/868,392

(22) Filed: Sep. 29, 2015

(65) Prior Publication Data

US 2016/0015260 A1 Jan. 21, 2016

Related U.S. Application Data

(63) Continuation of application No. PCT/JP2014/058781, filed on Mar. 27, 2014.

(30) Foreign Application Priority Data

Mar. 29, 2013 (JP) .................... 2013-074017

(51) Int. Cl.
*A61B 1/045* (2006.01)
*A61B 1/00* (2006.01)
(Continued)

(52) U.S. Cl.
CPC .......... *A61B 1/045* (2013.01); *A61B 1/00087* (2013.01); *A61B 1/00135* (2013.01);
(Continued)

(58) Field of Classification Search
CPC ......... A61B 34/77; A61B 34/35; A61B 34/32; A61B 2034/301; A61B 1/00147;
(Continued)

(56) References Cited

U.S. PATENT DOCUMENTS 5,558,619 A * 9/1996 Kami ................. A61B 1/00006
600/106
5,762,458 A * 6/1998 Wang .................... B25J 9/1689
414/1
(Continued)

FOREIGN PATENT DOCUMENTS

EP 2979608 2/2016
JP 09-266882 10/1997
(Continued)

OTHER PUBLICATIONS

"The Extended European Search Report of European Counterpart Application", dated Feb. 24, 2016, pp. 1-10.
(Continued)

*Primary Examiner* — Timothy J Neal
*Assistant Examiner* — Jae Woo
(74) *Attorney, Agent, or Firm* — JCIPRNET

(57) ABSTRACT

An endoscopic surgery device that can easily acquire an image desired by a surgeon, and that has high operability. The endoscopic surgery device includes: an outer tube body; an endoscope insertion path that is provided inside the outer tube body; a treatment tool insertion path that is provided inside the outer tube body; a position sensor that detects a movement amount of the treatment tool insertion part with respect to the outer tube body; and a control unit that has a non-sensitive area where a range of an observation image is not changed if the movement amount of the treatment tool insertion part is within a predetermined range, and a sensitive area where the range of the observation image is varied in accordance with the movement amount of the treatment tool insertion part if the movement amount of the treatment tool insertion part is not within the predetermined range.

8 Claims, 13 Drawing Sheets

(51) Int. Cl.
*A61B 1/05* (2006.01)
*A61B 1/06* (2006.01)
*A61B 1/313* (2006.01)
*A61B 17/34* (2006.01)
*A61B 1/04* (2006.01)
*A61B 90/00* (2016.01)
*A61B 34/20* (2016.01)

(52) U.S. Cl.
CPC ............ *A61B 1/00154* (2013.01); *A61B 1/05* (2013.01); *A61B 1/0676* (2013.01); *A61B 1/3132* (2013.01); *A61B 17/3421* (2013.01); *A61B 1/04* (2013.01); *A61B 2017/3441* (2013.01); *A61B 2017/3445* (2013.01); *A61B 2017/3466* (2013.01); *A61B 2034/2065* (2016.02); *A61B 2090/0811* (2016.02)

(58) Field of Classification Search
CPC .............. A61B 1/00149; A61B 1/0016; A61B 1/00135; A61B 1/00154
USPC .......................................................... 600/117
See application file for complete search history.

(56) References Cited

U.S. PATENT DOCUMENTS

| | | | | |
|---|---|---|---|---|
| 5,855,583 | A * | 1/1999 | Wang | B25J 9/1689 318/568.11 |
| 6,063,095 | A * | 5/2000 | Wang | A61B 34/75 128/898 |
| 6,096,004 | A * | 8/2000 | Meglan | A61B 34/75 604/95.01 |
| 6,221,007 | B1 * | 4/2001 | Green | A61B 1/00052 600/104 |
| 6,238,384 | B1 * | 5/2001 | Peer | A61B 17/062 128/898 |
| 6,245,028 | B1 * | 6/2001 | Furst | A61B 10/0233 600/411 |
| 6,962,563 | B2 * | 11/2005 | Yasunaga | A61B 1/00149 600/114 |
| 9,131,957 | B2 * | 9/2015 | Skarbnik | A61B 17/3421 |
| 2007/0265502 | A1 * | 11/2007 | Minosawa | A61B 1/00177 600/173 |
| 2008/0154091 | A1 | 6/2008 | Dejima et al. | |
| 2009/0234223 | A1 * | 9/2009 | Onoda | A61B 5/06 600/424 |
| 2009/0275798 | A1 * | 11/2009 | Naito | A61B 1/00149 600/106 |
| 2011/0202068 | A1 * | 8/2011 | Diolaiti | B25J 9/161 606/130 |
| 2011/0245661 | A1 * | 10/2011 | Yoshie | A61B 1/04 600/424 |
| 2012/0182409 | A1 | 7/2012 | Moriyama et al. | |
| 2014/0135794 | A1 * | 5/2014 | Cau | A61B 34/37 606/130 |
| 2014/0135795 | A1 * | 5/2014 | Yanagihara | A61B 34/77 606/130 |
| 2015/0196228 | A1 * | 7/2015 | Akimoto | A61B 1/05 600/109 |
| 2016/0015245 | A1 * | 1/2016 | Iwasaka | A61B 17/3421 600/106 |
| 2016/0015255 | A1 * | 1/2016 | Dejima | A61B 1/00135 600/106 |
| 2016/0015256 | A1 * | 1/2016 | Iwasaka | A61B 17/3421 600/106 |
| 2016/0022118 | A1 * | 1/2016 | Dejima | A61B 1/00154 600/104 |
| 2016/0022122 | A1 * | 1/2016 | Dejima | A61B 1/00087 600/210 |
| 2016/0128547 | A1 * | 5/2016 | Ogawa | A61B 1/00133 600/107 |
| 2016/0174825 | A1 * | 6/2016 | Dejima | A61B 1/00135 600/104 |
| 2016/0175004 | A1 * | 6/2016 | Dejima | A61B 1/00135 600/114 |
| 2016/0175005 | A1 * | 6/2016 | Dejima | A61B 1/00135 600/114 |
| 2016/0175006 | A1 * | 6/2016 | Dejima | A61B 1/00112 600/114 |
| 2016/0302653 | A1 * | 10/2016 | Inoue | G01C 3/08 |
| 2016/0331208 | A1 * | 11/2016 | Kikuchi | A61B 90/57 |

FOREIGN PATENT DOCUMENTS

| | | |
|---|---|---|
| JP | 10-118076 | 5/1998 |
| JP | 10-314104 | 12/1998 |
| JP | 2004-041778 | 2/2004 |
| JP | 2004041778 A * | 2/2004 |
| JP | 2004-141486 | 5/2004 |
| JP | 2004-180858 | 7/2004 |
| JP | 3955126 | 8/2007 |
| JP | 2007-301378 | 11/2007 |
| JP | 2008-132352 | 6/2008 |
| JP | 2008-155030 | 7/2008 |
| WO | 2012035923 | 3/2012 |

OTHER PUBLICATIONS

"Written Opinion of the International Searching Authority of PCT/JP2014/058781", this report contains the following items: Form PCT/ISA237 (cover sheet), PCT/ISA237 (Box No. I) and PCT/ISA237 (Box No. V), dated Jun. 24, 2014, with English translation thereof, pp. 1-7.

"Second Office Action of China Counterpart Application" with English translation thereof, dated Feb. 20, 2017, p. 1-p. 14.

* cited by examiner (A)

(B)

ENDOSCOPIC SURGERY DEVICE

CROSS-REFERENCE TO RELATED APPLICATIONS

This application is a Continuation of PCT International Application No. PCT/JP2014/058781 filed on Mar. 27, 2014, which claims priority under 35 U.S.C. § 119(a) to Japanese Patent Application No. 2013-074017 filed on Mar. 29, 2013. Each of the above application(s) is hereby expressly incorporated by reference, in its entirety, into the present application.

BACKGROUND OF THE INVENTION

Field of the Invention

The present invention relates to an endoscopic surgery device, and particularly relates to an endoscopic surgery device that can operate an endoscope and a treatment tool which are inserted in a body cavity in interlock with each other.

Description of the Related Art

Recently, endoscopic surgery using an endoscope (rigid endoscope) such as a laparoscope is widely performed because invasion to a patient is small as compared with surgery in which laparotomy and thoracotomy, and so on, are performed. For example, in laparoscopic surgery, a trocar is inserted in multiple places of patient's abdomen, an endoscope, a treatment tool or the like is inserted in a body cavity using an insertion hole formed in the trocar as a guide, and various kinds of treatments are performed using the treatment tool while observing an observation image (endoscope image) by a monitor.

In general, a surgeon's hands are busy by the operation of treatment tools in endoscopic surgery. Therefore, the operation of an endoscope is performed by an assistant who is called a scopist. However, in a case where the assistant operates the endoscope, the surgeon has to sequentially give an instruction to the assistant, and there are problems that a work to correctly turn the direction of the endoscope to a direction desired by the surgeon is difficult and the surgeon suffers stress. Moreover, since the assistance performs an operation after the surgeon gives an instruction, there is a problem of taking time to perform a surgery. In addition, the assistant has to operate the endoscope so as not to obstruct the surgeon's surgery, and there is a problem that the operation is likely to become complicated.

Meanwhile, Japanese Patent Application Laid-Open No. 2007-301378 (PTL 1) discloses a technique that inserts a treatment tool and an endoscope from opening portions formed in different positions in a body wall into body cavities respectively in endoscopic surgery and synchronously moves the endoscope according to the movement of the treatment tool. According to this technique, since the endoscope synchronously moves according to the surgeon's operation of the treatment tool, the assistant's operation of the endoscope becomes unnecessary, the surgeon's stress with the assistant is eliminated, the surgeon can perform a surgery as desired, and therefore it is convenient. Moreover, in the technique disclosed in PTL 1, to prevent an observation image obtained by the endoscope from minutely moving and being difficult to be seen, it is determined whether the distal end of the treatment tool is in the inner region of the observation image or it is in a peripheral region, the visual field of the endoscope is not changed in a case where the distal end of the treatment tool exists in the inner region of the observation image, and the visual field of the endoscope is changed such that the distal end of the treatment tool comes to the center of the observation image in a case where the distal end of the treatment tool exists in the outer region. By this means, it becomes possible to prevent the image from being rather difficult to be seen due to the minute movement of the observation image in interlock with the minute movement of the treatment tool.

Moreover, Japanese Patent Application Laid-Open No. 2004-180858 (PTL 2) and Japanese Patent Application Laid-Open No. 2004-141486 (PTL 3) disclose a technique in which: two insertion holes are provided in an outer tube which penetrates through a body wall and is inserted in a body cavity; and the endoscope is inserted in one insertion hole and the treatment tool is inserted in the other insertion hole. According to this technique, low invasion is achieved because it is possible to reduce the number of opening portions formed in a body wall to insert the treatment tool and the endoscope in the body cavity.

SUMMARY OF THE INVENTION

However, in the technique disclosed in PTL 1, it is effective in a case where the distal end of the treatment tool moves in a direction orthogonal to the visual field direction of the endoscope, but, if a zoom device is moved in interlock with a back-and-forth movement in the axial direction of the treatment tool, the size of an observation target changes in interlock with the minute movement of the treatment tool, and there is a problem that a depth perception is difficult to be recognized.

Moreover, in PTL 2 and PTL 3, there is no technical idea of synchronously moving the endoscope and the treatment tool which are inserted in the same outer tube, and there is no description that suggests a problem caused when the endoscope and the treatment tool are moved in interlock with each other.

The present invention is made in view of such circumstances, and aims to provide an endoscopic surgery device with high operability that can easily obtain an image desired by a surgeon.

In order to achieve the object described above, an endoscopic surgery device in accordance with the present invention includes: a guide member configured to penetrate through a body wall to be inserted into a body cavity; an endoscope insertion path which is provided inside the guide member, and into which an endoscope configured to observe an inside of the body cavity is insertable in a back-and-forth movable manner; a treatment tool insertion path which is provided inside the guide member, and into which a treatment tool configured to inspect or treat a diseased part in the body cavity is insertable in a back-and-forth movable manner; detection means (detection unit) configured to detect a movement amount of the treatment tool with respect to the guide member when the treatment tool inserted into the treatment tool insertion path moves back and forth; and control means (control unit) including a non-sensitive area where a range of an observation image acquired by the endoscope is not changed if the movement amount of the treatment tool is within a predetermined range when the movement amount of the treatment tool is detected by the detection means, and a sensitive area where the range of the observation image is changed in accordance with the movement amount of the treatment tool if the movement amount of the treatment tool is not within the predetermined range.

In one aspect of the endoscopic surgery device in accordance with the present invention, the control means changes the range of the observation image in proportion to the movement amount of the treatment tool in the sensitive area.

In yet another aspect of the endoscopic surgery device in accordance with the present invention, the control means is endoscope movement control means (endoscope movement control unit) including: a non-sensitive area where the endoscope is not moved back and forth if the movement amount of the treatment tool is within the predetermined range when the movement amount of the treatment tool is detected by the detection means; and a sensitive area where the endoscope is moved back and forth in accordance with the movement amount of the treatment tool if the movement amount of the treatment tool is not within the predetermined range.

In addition, in yet another aspect of the endoscopic surgery device in accordance with the present invention, the control means is zoom control means (zoom control unit) including: a non-sensitive area where a magnification of the observation image is not changed if the movement amount of the treatment tool is within the predetermined range when the movement amount of the treatment tool is detected by the detection means; and a sensitive area where the magnification of the observation image is changed in accordance with the movement amount of the treatment tool if the movement amount of the treatment tool is not within the predetermined range.

Furthermore, in yet another aspect of the endoscopic surgery device in accordance with the present invention, the endoscope includes a zoom lens configured to be movable in an optical axis direction, and the zoom control means includes optical zoom control means (optical zoom control unit) configured to change the magnification of the observation image by allowing the zoom lens to move in the optical axis direction based on a detection result by the detection means.

In addition, in yet another aspect of the endoscopic surgery device in accordance with the present invention, the zoom control means includes electronic zoom control means (electronic zoom control unit) configured to change the magnification of the observation image acquired by the endoscope by performing electronic variable magnification processing to the observation image based on a detection result by the detection means.

Further, in yet another aspect of the endoscopic surgery device in accordance with the present invention, the detection means includes: calculation means configured to calculate the movement amount of the treatment tool in the observation image; and conversion means configured to convert the movement amount of the treatment tool in the observation image calculated by the calculation means into an actual movement amount.

According to the present invention, a range of an observation image acquired by an endoscope is changed with an allowance (play) with respect to a back-and-forth movement of a treatment tool. Accordingly, it is possible to prevent a size of an observation target from changing in a case where an insertion part of the treatment tool is slightly displaced in an axial direction (in a case of a back-and-forth movement of a small amplitude). As a result, a depth perception can be properly kept and a stable observation image can be provided. In addition, in a case where the treatment tool is largely displaced in the axial direction (in a case of a back-and-forth movement of a large amplitude), since the range of the observation image acquired by the endoscope is changed in interlock with the displacement, a size of the observation target changes in response to operation of the treatment tool. As a result, it is possible to easily acquire an image desired by a surgeon and operability is improved.

DETAILED DESCRIPTION OF THE EMBODIMENTS

Hereinafter, referring to accompanying drawings, a preferable embodiment of the present invention will be described in detail. Every drawing shows a main part that is emphasized for explanation, and is sometimes shown by a different dimension from an actual dimension.

First Embodiment

Figure 1:
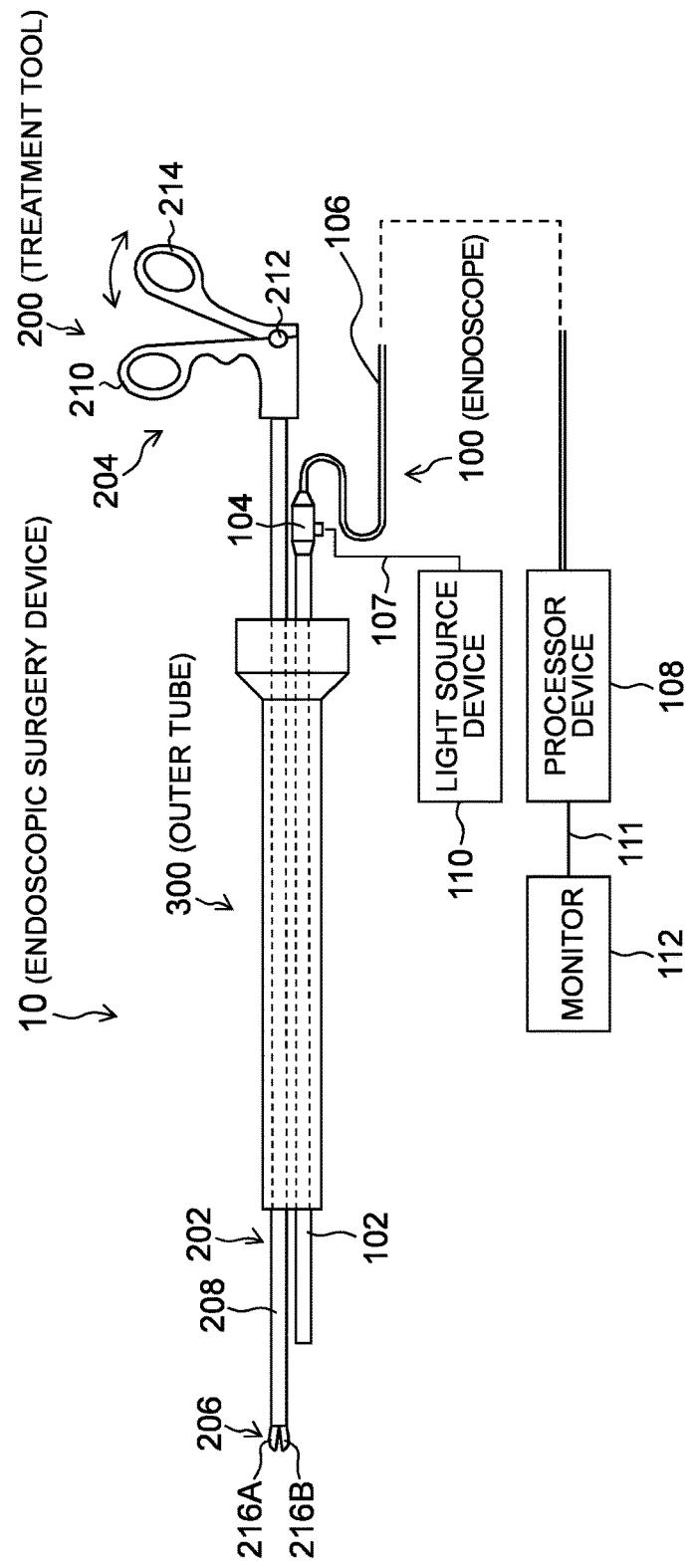
FIG. 1 is a schematic configuration diagram showing an endoscopic surgery device in accordance with a first embodiment.

FIG. 1 is a schematic configuration diagram showing an endoscopic surgery device according to the first embodiment. As shown in FIG. 1, an endoscopic surgery device 10 of the present embodiment includes an endoscope 100 that observes the inside of a body cavity of a patient, a treatment tool 200 for inspecting or treating a diseased part in the body cavity of the patient, and an outer tube 300 that guides the endoscope 100 and the treatment tool 200 into the body cavity.

The endoscope 100 is a rigid endoscope such as a laparoscope, for example, and includes an elongated insertion part (hereinafter referred to as an "endoscope insertion part") 102 to be inserted into a body cavity, and an operation part 104 connected to a proximal end side of the endoscope insertion part 102. A universal cable 106 is connected to the operation part 104, and a processor device 108 is detachably connected to a top end of the universal cable 106 through a connector (not shown). In addition, the processor device 108 is connected to a monitor 112 through a cable 111. Further, a light cable 107 extends from a side portion of the operation part 104, and a connector (not shown) is provided at a top end of the light cable 107. The connector is detachably connected to a light source device 110.

Figure 2:
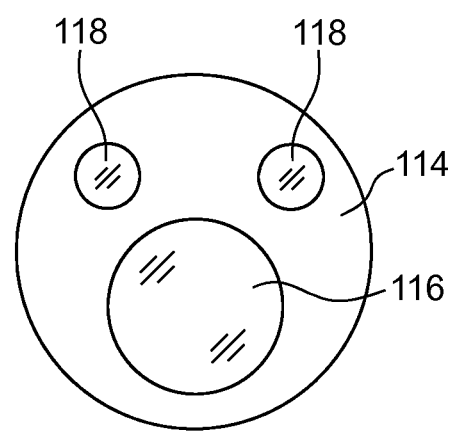
FIG. 2 is a plan view showing a distal end surface of an insertion part of an endoscope.

As shown in FIG. 2, an observation window 116 and an illumination windows 118 and 118 are provided in a distal end surface 114 of the endoscope insertion part 102.

Behind the observation window 116, there are arranged an objective lens of an observation optical system, and an imaging element arranged at an imaging position of the objective lens, such as a charge coupled device (CCD) and a complementary metal-oxide semiconductor (CMOS). A signal cable (not shown) is connected to a substrate supporting the imaging element. The signal cable is inserted into the endoscope insertion part 102, the operation part 104, the universal cable 106, and the like, shown in FIG. 1, to extend to a connector (not shown), and then connected to the processor device 108. An observation image captured through the observation window 116 is imaged in a receiving surface of the imaging element to be converted into an electric signal (an imaging signal), and then the electric signal is outputted to the processor device 108 through the signal cable to be converted into a video signal. Then, the video signal is outputted to the monitor 112 connected to the processor device 108 so that the observation image (endoscope image) is displayed in a screen of the monitor 112.

Behind the illumination windows 118 and 118 of FIG. 2, an emission end of a light guide (not shown) is arranged. The light guide is inserted into the endoscope insertion part 102, the operation part 104, and the light cable 107, shown in FIG. 1, and an incident end thereof is arranged in a connector (not shown). Thus, the connector is coupled to the light source device 110, so that illumination light emitted from the light source device 110 is transmitted to the illumination windows 118 and 118 through the light guide to be emitted forward through the illumination windows 118 and 118. In FIG. 2, although the two illumination windows 118 and 118 are provided in the distal end surface 114 of the endoscope insertion part 102, the number of the illumination windows 118 is not limited, and the number may be one, or three or more.

As shown in FIG. 1, the treatment tool 200 is composed of forceps, for example, and includes an elongated insertion part (hereinafter referred to as a "treatment tool insertion part") 202 to be inserted into a body cavity, an operation part 204 that is provided on a proximal end side of the treatment tool insertion part 202 to be held by a surgeon, and a treatment part 206 that is provided on a distal end side of the treatment tool insertion part 202 to be movable by operation of the operation part 204.

The treatment tool insertion part 202 is provided with a cylindrical sheath 208 and an operation shaft (not shown) that is movably inserted into the sheath 208 in an axis direction. In addition, the operation part 204 is provided with a fixed handle 210 and a movable handle 214 that is rotatably coupled to the fixed handle 210 through a rotation pin 212. Further, a proximal end of the operation shaft is coupled to the movable handle 214.

The treatment part 206 is provided with a pair of holding members 216A and 216B that can be opened and closed. The holding members 216A and 216B are coupled to a distal end of the operation shaft through a drive mechanism (not shown). Then, the holding members 216A and 216B of the treatment part 206 are opened or closed through the operation shaft and the drive mechanism, according to rotation operation of the movable handle 214 of the operation part 204.

The treatment tool 200 is not limited to forceps, and another treatment tool, such as a laser probe, a suture instrument, an electric knife, a needle holder, and an ultrasound aspirator, for example, may be used.

Figure 3:
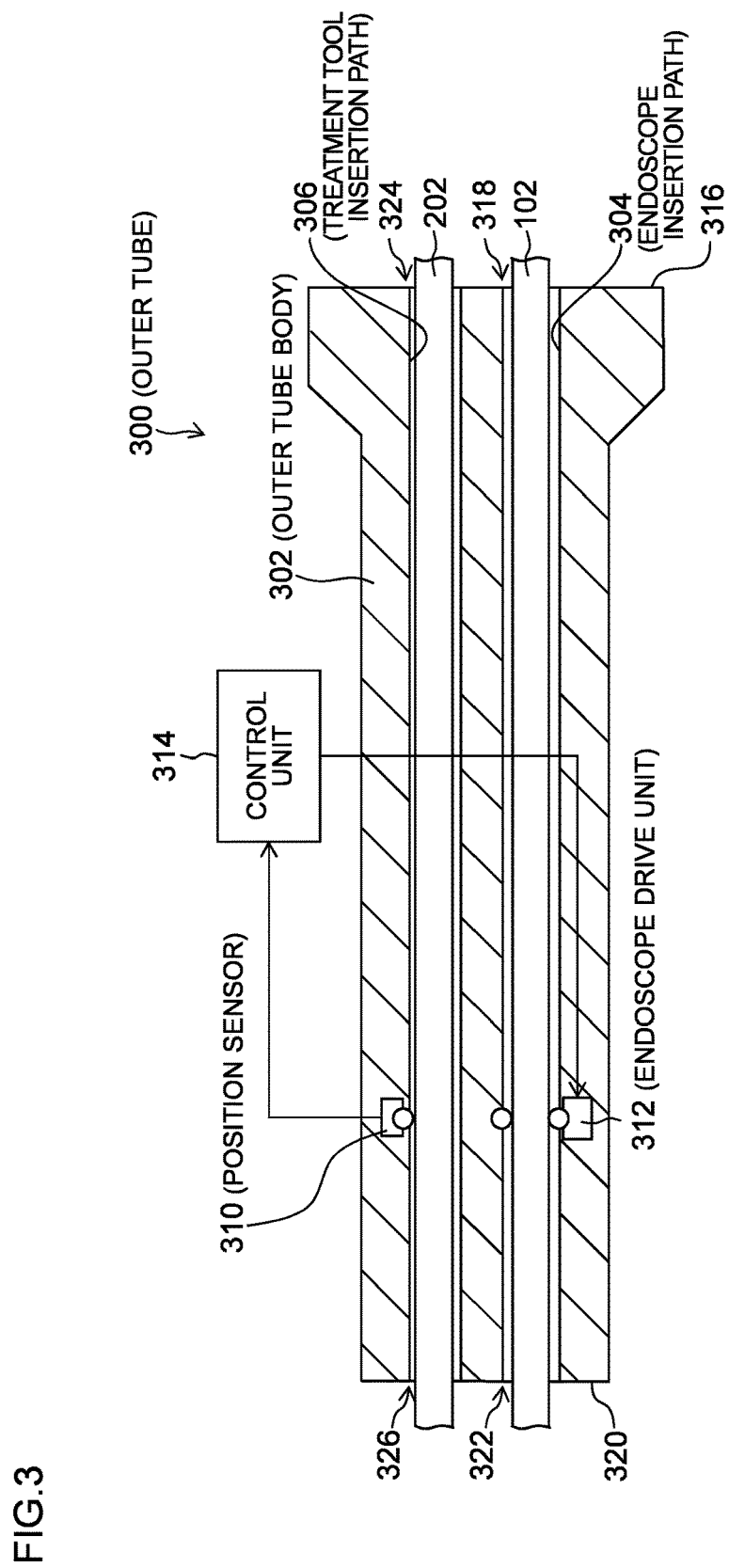
FIG. 3 is a schematic diagram showing an internal structure of an outer tube.

FIG. 3 is a schematic diagram showing an internal structure of the outer tube 300.

As shown in FIG. 3, the outer tube 300 includes an outer tube body 302, an endoscope insertion path 304, a treatment tool insertion path 306, a position sensor 310, an endoscope drive unit 312, and a control unit 314.

The outer tube body 302 is a guide member that penetrates through a body wall of a patient to be inserted into a body cavity. The endoscope insertion path 304 and the treatment tool insertion path 306 are provided inside the outer tube body 302.

The endoscope insertion path 304 is formed so as to penetrate through the outer tube body 302 along the axial direction of the outer the body 302, and is configured as an insertion path in which the endoscope insertion part 102 can be inserted (insertable) in a back and forth movable manner. The endoscope insertion path 304 communicates with an endoscope entry port 318 opened to a proximal end face 316 of the outer tube body 302 and communicates with an endoscope exit port 322 opened to a distal end surface 320 of the outer tube body 302. Accordingly, a distal end of the endoscope insertion part 102 inserted into the endoscope entry port 318 is delivered out from the endoscope exit port 322 through the endoscope insertion path 304.

The treatment tool insertion path 306 is formed so as to penetrate through the outer tube body 302 along the axial direction of the outer tube body 302, and is configured so that the treatment tool insertion part 202 can be inserted in the treatment tool insertion path 306 in a back and forth movable manner. The treatment tool insertion path 306 communicates with a treatment tool entry port 324 opened to the proximal end face 316 of the outer tube body 302 and communicates with a treatment tool exit port 326 opened to the distal end surface 320 of the outer tube body 302. Accordingly, the treatment part 206 that is a distal end of the treatment tool insertion part 202, inserted into the treatment tool entry port 324, is delivered out from the treatment tool exit port 326 through the treatment tool insertion path 306.

Each of the endoscope insertion path 304 and the treatment tool insertion path 306 is provided with a check valve and a seal member, which are not shown, to secure air tightness in a body cavity. Accordingly, it is possible to prevent carbon dioxide gas injected into the body cavity from flowing out from the body cavity through the endoscope insertion path 304 and the treatment tool insertion path 306. In addition, a stopper portion (not shown) for preventing the slider 308 described later from falling out is provided in an end part of each of the distal end side and the proximal end side of the treatment tool insertion path 306.

The position sensor 310 detects the movement amount of the treatment tool insertion part 202 inserted into the treatment tool insertion path 306. That is, the position sensor 310 is configured as detection means that detects the movement amount of the treatment tool insertion part 202 with respect to the outer tube body 302 when the treatment tool insertion part 202 is moved back and forth. As the position sensor 310, a position sensor, such as a potentiometer, an encoder, and a magnetic resistance (MR) sensor, can be used. For example, as shown in FIG. 3, by detecting an rotation amount of a rotation body (roller) configured to be rotatable with respect to the back-and-forth movement of the treatment tool insertion part 202 using a rotary encoder, a potentiometer, or the like, it is possible to detect the movement amount of the treatment tool insertion part 202. The detection result of the position sensor 310 is output to the control unit 314.

Here, it is assumed that the movement amount of the treatment tool insertion part 202 detected by the position sensor 310 has a positive or negative value depending on a movement direction. Specifically, the movement amount of the treatment tool insertion part 202 is indicated as a positive value in a case where the treatment tool insertion part 202 moves to a diseased part side (a distal end side, or a forward side) in a body cavity, and the movement amount of the treatment tool insertion part 202 is indicated as a negative value in a case where the treatment tool insertion part 202 moves to a hand side (a proximal end side, or a backward side) opposite to the diseased part side.

The endoscope drive unit 312 is drive means that moves the endoscope insertion part 102 inserted into the endoscope insertion path 304 back and forth, and that is composed of a motor, a gear, and the like, for example. The endoscope drive unit 312 moves the endoscope insertion part 102 back and forth on the basis of a control signal outputted from the control unit 314. Although the endoscope drive unit 312 is built in the outer tube body 302 in the present example, but it is not limited to this, the endoscope may be one which moves back and forth the endoscope insertion part 102 from outside of the outer tube body 302.

The control unit 314 is endoscope movement control means that controls the back-and-forth movement of the endoscope insertion part 102 through the endoscope drive unit 312 on the basis of a detection result of the position sensor 310. Specifically, the control unit 314 performs control in accordance with a graph shown in FIG. 4.

Figure 4:
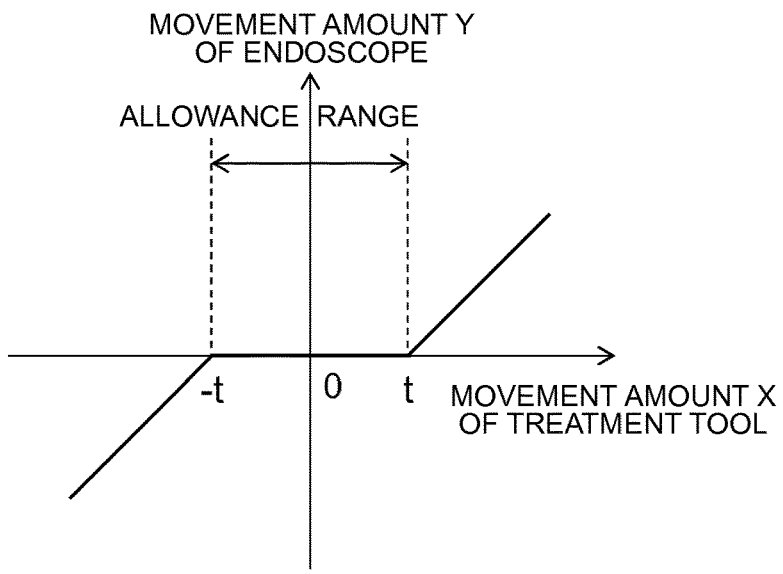
FIG. 4 is a graph showing a relationship between a movement amount of a treatment tool insertion part and a movement amount of an endoscope insertion part.

FIG. 4 is a graph showing a relationship between a movement amount X of the treatment tool insertion part 202 and a movement amount Y of the endoscope insertion part 102. As shown in FIG. 4, in a case where the movement amount X of the treatment tool insertion part 202 is within a predetermined allowance range in which a movement amount X of 0 (zero) is set as a center, the control unit 314 performs control to set the movement amount Y of the endoscope insertion part 102 to 0 (zero). That is, in a case where the movement amount X of the treatment tool insertion part 202 satisfies $-t \leq X \leq t$ (here, $t>0$ is assumed), the endoscope insertion part 102 is not moved back and forth.

On the other hand, in a case where the movement amount X of the treatment tool insertion part 202 is not within the above-mentioned allowance range, the control unit 314 performs control to move the endoscope insertion part 102 back and forth in interlock with the back-and-forth movement of the treatment tool insertion part 202. Specifically, the control unit 314 performs control to set a value obtained by adding an allowance amount t to the movement amount X of the treatment tool insertion part 202 or a value obtained by subtracting the allowance amount t from the movement amount X of the treatment tool insertion part 202, as the movement amount Y of the endoscope insertion part 102.

Accordingly, it becomes possible to move the endoscope insertion part 102 back and forth in interlock with the back-and-forth movement of the treatment tool insertion part 202, with an allowance with respect to the back-and-forth movement of the treatment toll insertion part 202. The control unit 314 may be built in the outer tube body 302, or may be connected to the outside of the outer tube body 302 through wiring.

Figure 5:
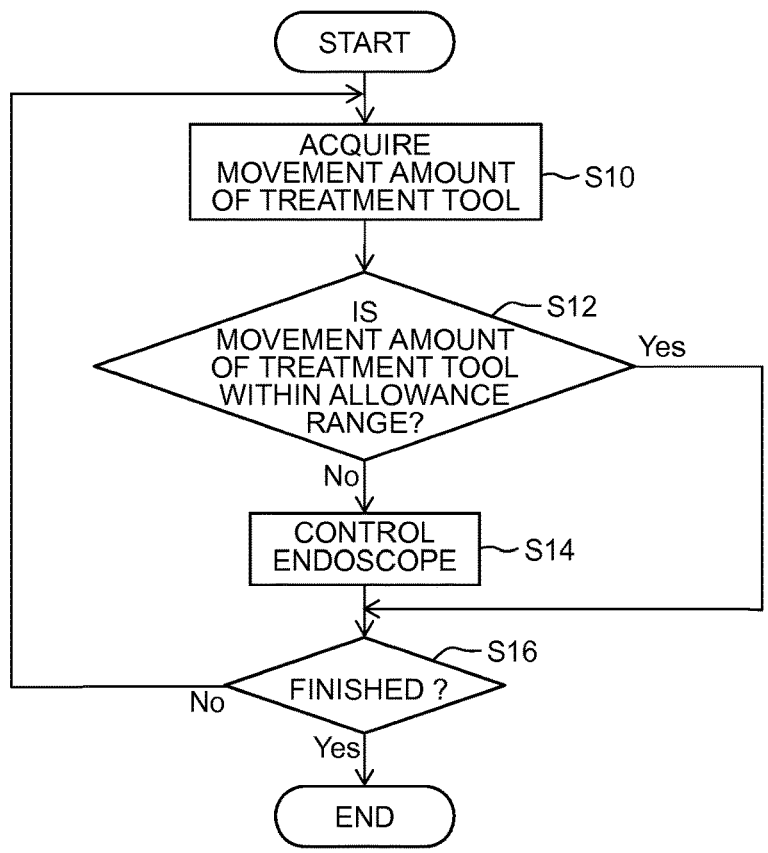
FIG. 5 is a flow chart showing an example of processing performed by a control unit.

FIG. 5 is a flow chart showing an example of processing performed by the control unit 314.

First, the control unit 314 acquires the movement amount of the treatment tool insertion part 202 detected by the position sensor 310 (step S10).

Next, the control unit 314 determines whether the movement amount of the treatment tool insertion part 202 acquired from the position sensor 310 is within a predetermined allowance range or not (step S12). If the movement amount of the treatment tool insertion part 202 is within the allowance range, processing proceeds to step S16 by skipping step S14.

On the other hand, if the movement amount of the treatment tool insertion part 202 is not within the allowance range, as described above, the control unit 314 performs control in accordance with the graph shown in FIG. 4 to move the endoscope insertion part 102 back and forth in interlock with the back-and-forth movement of the treatment tool insertion part 202 (step S14).

Next, the control unit 314 determines whether the operation is finished or not (step S16). If it is determined that the operation is not finished, the processing returns to step S10 so that the same processing is performed. On the other hand, if it is determined that the operation is finished, control by the control unit 314 is finished.

As a method of determining whether the operation is finished or not, there may be provided a sensor for detecting whether the endoscope insertion part 102 or the treatment tool insertion part 202 is inserted into the outer tube body 302 or not, for example, so that it is determined whether the operation is finished on the basis of a detection result of the sensor. Or, an ON/OFF switch operable by hand may be provided so that it is determined whether the operation is finished in response to an operation state of the ON/OFF switch.

Figure 6:
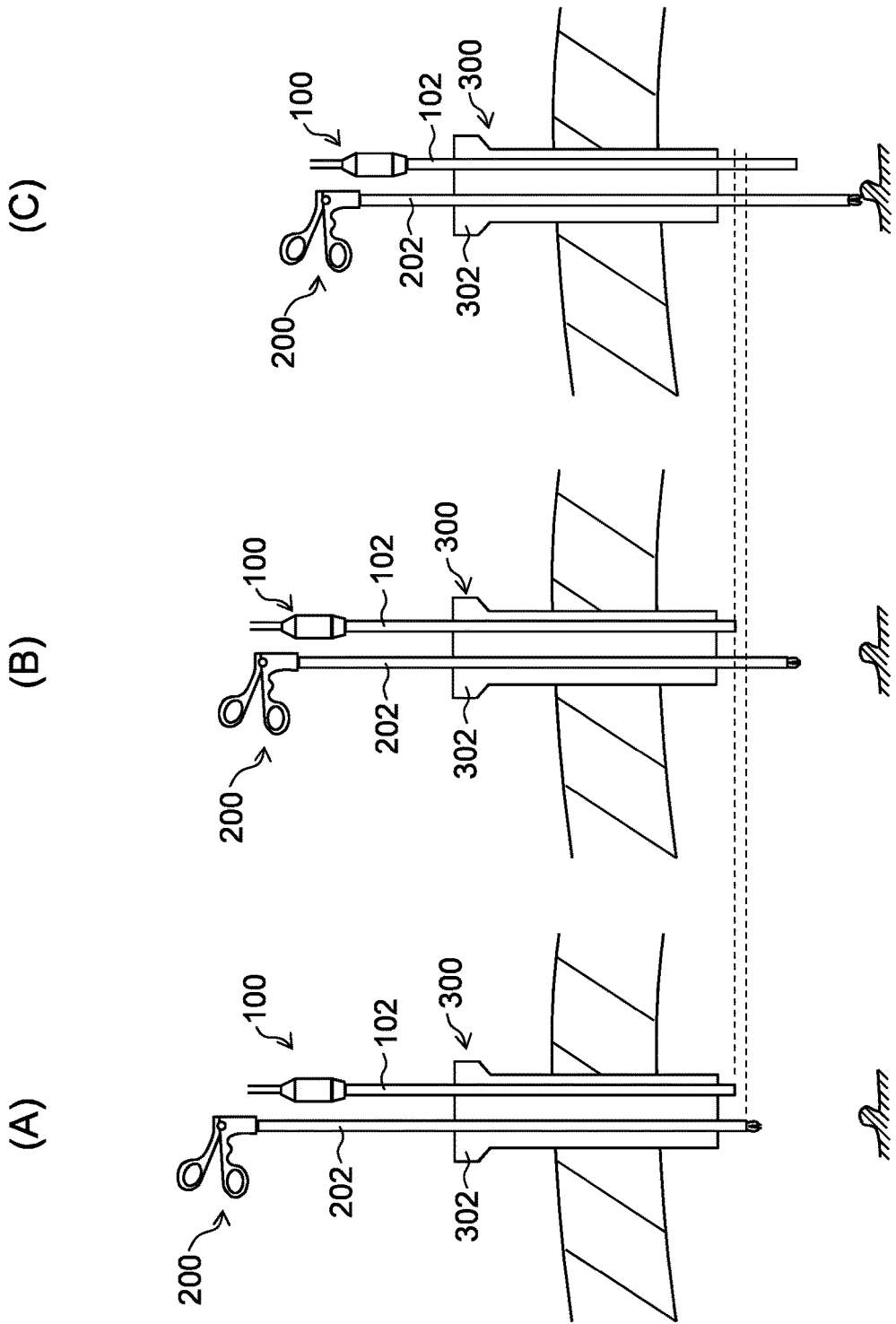
FIG. 6 is a diagram showing a state where an insertion part of a treatment tool is pushed into a diseased part side in a body cavity from a hand side.
Figure 7:
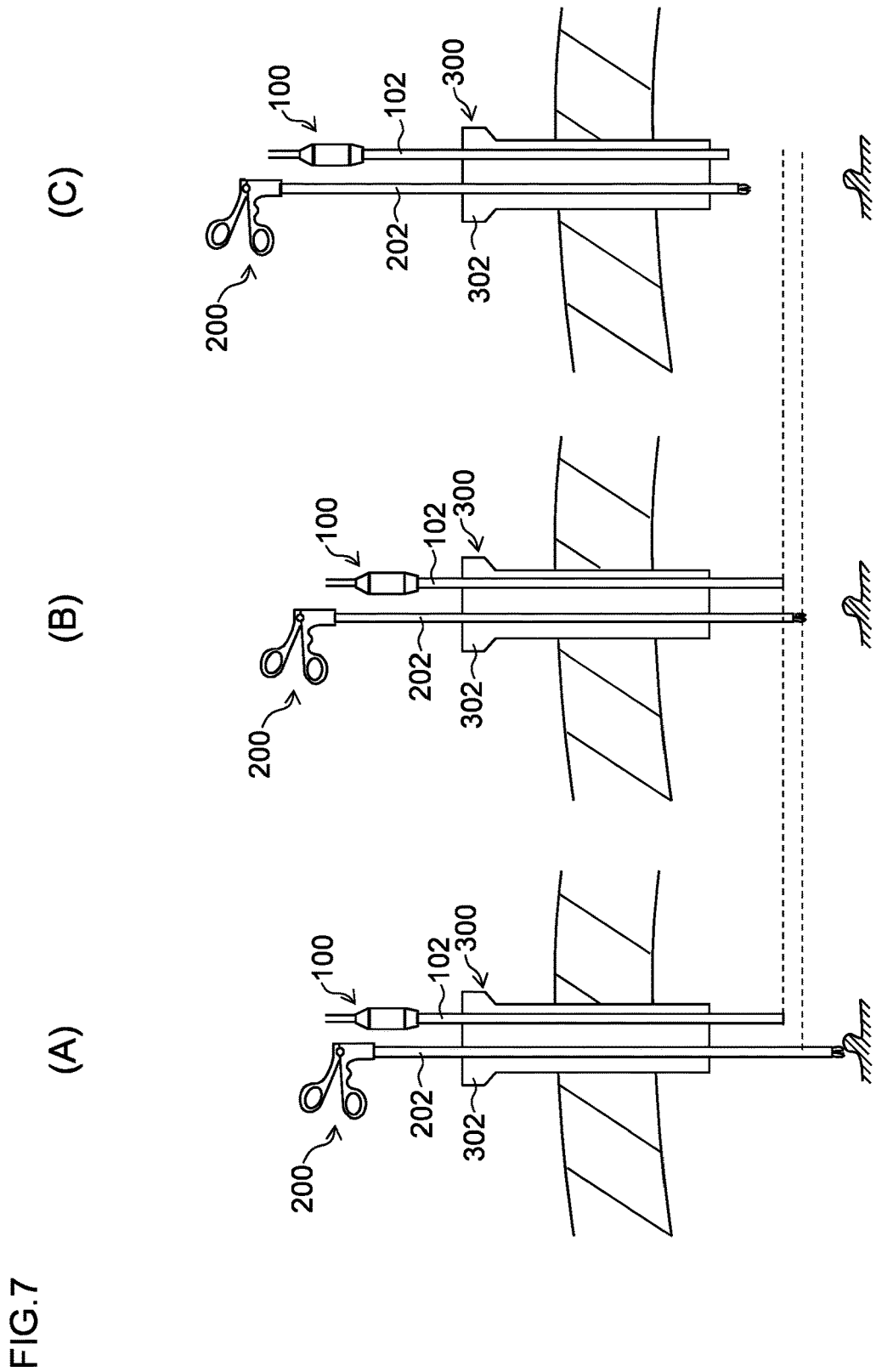
FIG. 7 is a diagram showing a state where an insertion part of a treatment tool is pulled from a diseased part side in a body cavity to a hand side.

Each of FIGS. 6 and 7 is an illustration showing a state where the endoscopic surgery device 10 of the present embodiment is operated. FIG. 6 is a diagram showing a state where the treatment tool insertion part 202 is pushed into a diseased part side in a body cavity from a hand side. FIG. 7 is a diagram showing a state where the treatment tool insertion part 202 is pulled from a diseased part side in a body cavity to a hand side. Hereinafter, first a preparation process for starting operation of the endoscopic surgery device 10 will be described, and then action at the time when the operation shown in FIGS. 6 and 7 is performed will be described.

First, as the preparation process for starting operation of the endoscopic surgery device 10, the outer tube body 302 is inserted into a body cavity through an opening (incised wound) formed in a body wall, and then the treatment tool insertion part 202 is inserted into the treatment tool insertion path 306 from the treatment tool entry port 324 so that a distal end of the treatment tool insertion part 202 is delivered out from the treatment tool exit port 326.

Subsequently, the endoscope insertion part 102 is inserted into the endoscope insertion path 304 from the endoscope entry port 318, and then a distal end of the endoscope insertion part 102 is delivered out from the endoscope exit port 322. At this time, the endoscope insertion part 102 is adjusted so as to arrange a position of the distal end of the endoscope insertion part 102, at least, on the back side (on the hand side opposite to the diseased part side in the body cavity) of a position of the distal end of the treatment tool insertion part 202. Accordingly, a state of the treatment part 206 arranged at the distal end of the treatment tool insertion part 202 can be observed with the endoscope 100.

After the preparation process is performed in this way, the endoscopic surgery device 10 becomes a state where operation thereof can be started. Here, insertion procedure of the endoscope 100 and the treatment tool 200 into the outer tube body 302 is not limited to the order described above, and the treatment tool 200 may be inserted followed by the endoscope 100.

Next, a state where the treatment tool insertion part 202 is pushed into the diseased part side in the body cavity from the hand side will be described with reference to FIG. 6.

First, in a case where the treatment tool insertion part 202 is slightly displaced in the axial direction (in a case of a back-and-forth movement of a small amplitude) as a state changes from that shown in portion (A) of FIG. 6 to a state shown in portion (B) of FIG. 6, the control unit 314 does not allow the endoscope insertion part 102 to move back and forth. Thus, a range of an observation image displayed in the monitor 112 does not change. As a result, it is possible to prevent a size of an observation target from changing in accordance with a slight displacement of the treatment tool insertion part 202, and thus a depth perception can be properly kept to enable a stable observation image to be acquired.

On the other hand, in a case where the treatment tool insertion part 202 is largely displaced in the axial direction (in a case of a back-and-forth movement of a large amplitude) as a state changes from that shown in portion (A) of FIG. 6 to a state shown in portion (C) of FIG. 6, the control unit 314 allows the endoscope insertion part 102 to move back and forth in interlock with the back-and-forth movement of the treatment tool insertion part 202. Accordingly, a range of an observation image displayed in the monitor 112 is continuously changed so as to follow the back-and-forth movement of the treatment tool insertion part 202. As a result, since a size of an observation target is changed in response to operation of the treatment tool 200, it becomes possible to easily acquire an image desired by a surgeon.

The same applies to a case where the treatment tool insertion part 202 is pulled from the diseased part side in the body cavity to the hand side.

That is, in a case where the treatment tool insertion part 202 is slightly displaced in the axial direction (in a case of a back-and-forth movement of a small amplitude) as a state changes from that shown in portion (A) of FIG. 7 to a state shown in portion (B) of FIG. 7, the control unit 314 does not allow the endoscope insertion part 102 to move back and forth, so that a range of an observation image displayed in the monitor 112 does not change. As a result, it is possible to prevent a size of an observation target from changing in accordance with a slight displacement of the treatment tool insertion part 202, and thus a depth perception can be properly kept to enable a stable observation image to be acquired.

On the other hand, in a case where the treatment tool insertion part 202 is largely displaced in the axial direction (in a case of a back-and-forth movement of a large amplitude) as a state changes from that shown in portion (A) of FIG. 7 to a state shown in portion (C) of FIG. 7, the control unit 314 allows the endoscope insertion part 102 to move back and forth in interlock with the back-and-forth movement of the treatment tool insertion part 202. Accordingly, a range of an observation image displayed in the monitor 112 is continuously changed so as to follow the back-and-forth movement of the treatment tool insertion part 202. As a result, since a size of an observation target is changed in response to operation of the treatment tool 200, it becomes possible to easily acquire an image desired by a surgeon.

Here, it is preferable to control the back-and-forth movement of the endoscope insertion part 102 so that a range of an observation image displayed in the monitor 112 is always constant even if the treatment tool insertion part 202 is moved back and forth.

As above, in the present embodiment, in a state where the endoscope insertion part 102 and the treatment tool insertion part 202 are arranged in parallel, since the endoscope insertion part 102 moves back and forth with an allowance with respect to the back-and-forth movement of the treatment tool insertion part 202, a range of an observation image acquired by the endoscope 100 is changed. Accordingly, it is possible to prevent a size of an observation target from changing in a case where the treatment tool insertion part 202 is slightly displaced in the axial direction (in a case where the back-and-forth movement of a small amplitude is performed). As a result, a depth perception can be properly kept to enable a stable observation image to be provided. In addition, in a case where the treatment tool insertion part 202 is largely displaced in the axial direction (in a case where the back-and-forth movement of a large amplitude is performed), since a range of an observation image is changed in interlock with the displacement, a size of the observation target changes in response to the operation of the treatment tool 200. As a result, it is possible to easily acquire an image desired by a surgeon and operability is improved.

Particularly in the present embodiment, in a case where the treatment tool insertion part 202 is largely displaced in the axial direction, since a range of an observation image is continuously changed in interlock with the back-and-forth movement of the treatment tool insertion part 202 without being discretely changed, the observation image smoothly changes in response to operation of the treatment tool 200. As a result, a surgeon can operate the treatment tool 200 without a sense of discomfort while viewing the observation image.

In addition, since the surgeon can change a range of an observation image acquired by the endoscope 100 by only operating the treatment tool 200 without releasing its hand from the treatment tool 200, operation of the endoscope 100 by an assistant becomes unnecessary. As a result, it is possible to display a part where the surgeon wants to view without stress, and eliminate stress caused by an assistant and instruction time for the assistant, so that operative procedure becomes easy to enable operative time to be shortened.

Second Embodiment

Next, a second embodiment of the present invention will be described. Hereinafter, description of a portion common to the first embodiment is omitted, and the present embodiment will be described with a focus on characteristics thereof.

Figure 8:
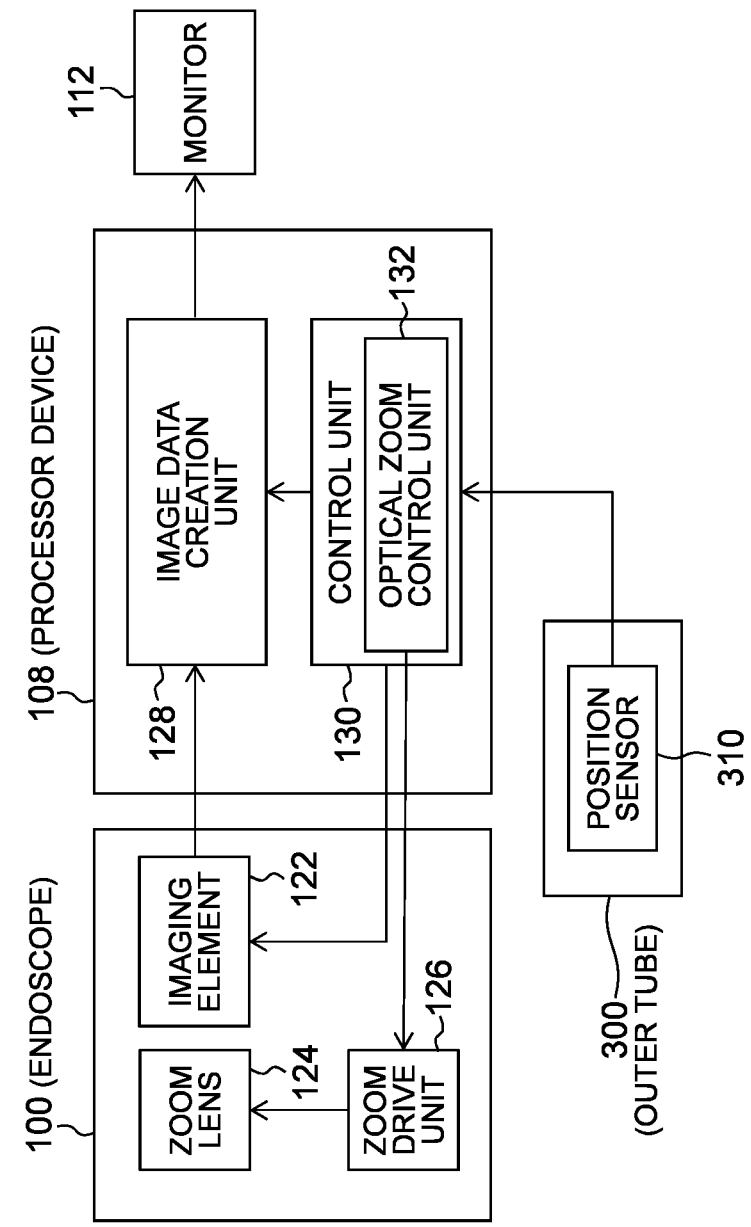
FIG. 8 is a functional block diagram showing a configuration of a main part of an endoscopic surgery device in accordance with a second embodiment.

FIG. 8 is a schematic configuration diagram showing a structure of a main part of an endoscopic surgery device according to the second embodiment. In FIG. 8, a component that is identical with or corresponds to that of Figures shown above is designated by the same reference numeral as that of the Figures.

In the second embodiment, as shown in FIG. 8, an observation optical system of the endoscope 100 includes a zoom lens 124 as a part of lenses thereof. The zoom lens 124 is configured to be movable in an optical axis direction with a zoom drive unit 126. The zoom lens 124 is moved in the optical axis direction to change a focal length so that magnification of a subject image imaged in an imaging element 122 is changed. As a result, magnification of an observation image displayed in the monitor 112 is changed.

The processor device 108 is provided with an image data creation unit 128 that applies various kinds of signal processing, such as color separation, color interpolation, gain correction, white balance adjustment, and gamma correction, to an imaging signal outputted from the imaging element 122 of the endoscope 100 to create image data. The image data created by the image data creation unit 128 is converted into a video signal in accordance with a signal type corresponding to the monitor 112 to be outputted to the monitor 112. Accordingly, an observation image (endoscope image) is displayed in the monitor 112.

In addition, the processor device 108 is provided with a control unit 130 that integrally controls the processor device 108 and each unit of the endoscope 100. The control unit 130 includes an optical zoom control unit 132 as optical zoom control means. The optical zoom control unit 132 controls the zoom lens 124 so as to move in the optical axis direction with the zoom drive unit 126 on the basis of a detection result (that is, a movement amount of the treatment tool insertion part 202) of a position sensor 310 provided in the outer tube 300 to change magnification of an observation image. Specifically, the optical zoom control unit 132 does not allow the zoom lens 124 to move if the movement amount of the treatment tool insertion part 202 is within an allowance range, and allows the zoom lens 124 to move in interlock with the back-and-forth movement of the treatment tool insertion part 202 if the movement amount of the treatment tool insertion part 202 is not within the allowance range.

By the configuration described above, in a case where the treatment tool insertion part 202 is slightly displaced in the axial direction (in a case of a back-and-forth movement of a small amplitude is performed), the zoom lens 124 is not driven. Thus, a range of an observation image displayed in the monitor 112 does not change. As a result, it is possible to prevent a size of an observation target from changing, and a depth perception can be properly kept to enable a stable observation image to be provided. On the other hand, in a case where the treatment tool insertion part 202 is largely displaced in the axial direction (in a case of a back-and-forth movement of a large amplitude is performed), the zoom lens 124 is driven in interlock with the back-and-forth movement of the treatment tool insertion part 202. As a result, since a range of an observation image displayed in the monitor 112 is continuously changed so as to follow the back-and-forth movement of the treatment tool insertion part 202, a size of an observation target changes in response to operation of the treatment tool 200, and thus an image desired by a surgeon can be easily acquired and operability is improved.

In addition, it is preferable to control drive of the zoom lens 124 so that a range of an observation image displayed in the monitor 112 is always constant even if the treatment tool insertion part 202 is moved back and forth.

Thus, also in the second embodiment, the same effect as that of the first embodiment can be obtained. In addition, since it is unnecessary to provide means (such as the endoscope drive unit 312) for moving the endoscope insertion part 102 inserted into the endoscope insertion path 304 back and forth, a structure of the outer tube body 302 becomes simple to enable a diameter of the outer tube body 302 to be reduced.

Third Embodiment

Next, a third embodiment of the present invention will be described. Hereinafter, description of a portion common to the first and second embodiments is omitted, and the present embodiment will be described with a focus on characteristics thereof.

Figure 9:
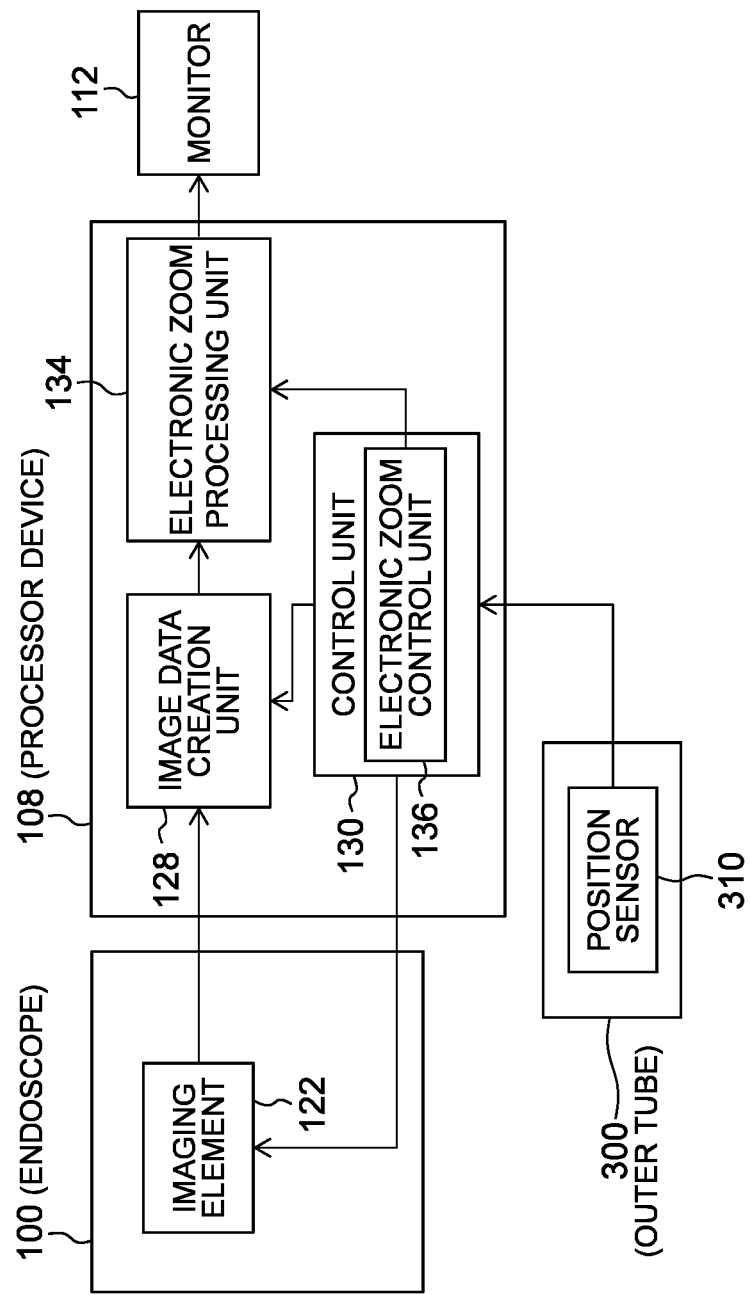
FIG. 9 is a functional block diagram showing a configuration of a main part of an endoscopic surgery device in accordance with a third embodiment.

FIG. 9 is a functional block diagram showing a configuration of a main part of an endoscopic surgery device in accordance with the third embodiment. In FIG. 9, a component that is identical with or corresponds to that of Figures shown above is designated by the same reference numeral as that of the Figures.

In the third embodiment, as shown in FIG. 9, the processor device 108 includes an electronic zoom processing unit 134 that extracts a part of the image data created by the image data creation unit 128 to electronically perform variable magnification processing.

The control unit 130 includes an electronic zoom control unit 136 as electronic zoom control means. The electronic zoom control unit 136 changes a magnification of the observation image displayed in the monitor 112 by controlling the electronic zoom processing unit 134 on the basis of a detection result (that is, a movement amount of the treatment tool insertion part 202) of the position sensor 310 provided in the outer tube 300. Specifically, the electronic zoom control unit 136 does not allow the electronic zoom processing unit 134 to perform variable magnification processing if the movement amount of the treatment tool insertion part 202 is within the allowance range, and allows the electronic zoom processing unit 134 to perform the variable magnification processing in interlock with the back-and-forth movement of the treatment tool insertion part 202 if the movement amount of the treatment tool insertion part 202 is not within the allowance range.

By the configuration described above, in a case where the treatment tool insertion part 202 is slightly displaced in the axial direction (in a case of a back-and-forth movement of a small amplitude is performed), since the electronic zoom processing unit 134 does not perform the variable magnification processing, a range of an observation image displayed in the monitor 112 does not change. As a result, it is possible to prevent a size of an observation target from changing, so that a depth perception can be properly kept and a stable observation image can be provided. On the other hand, in a case where the treatment tool insertion part 202 is largely displaced in the axial direction (in a case of a back-and-forth movement of a large amplitude is performed), the electronic zoom processing unit 134 performs the variable magnification processing in interlock with the back-and-forth movement of the treatment tool insertion part 202. As a result, since a range of an observation image displayed in the monitor 112 is continuously changed so as to follow the back-and-forth movement of the treatment tool insertion part 202, a size of an observation target changes in response to operation of the treatment tool 200 to enable an image desired by a surgeon to be easily acquired and operability is improved.

Here, it is preferable to control the variable magnification processing by the electronic zoom processing unit 134 so that a range of an observation image displayed in the monitor 112 is always constant even if the treatment tool insertion part 202 is moved back and forth.

Thus, also in the third embodiment, the same effect as that of the first embodiment can be obtained. In addition, since it is unnecessary to provide means (such as the endoscope drive unit 312) for moving the endoscope insertion part 102 inserted into the endoscope insertion path 304 back and forth, a structure of the outer tube body 302 becomes simple to enable a diameter of the outer tube body 302 to be reduced.

Fourth Embodiment

Next, a fourth embodiment of the present invention will be described. Hereinafter, description of a portion common to the first to third embodiments is omitted, and the present embodiment will be described with a focus on characteristics thereof.

Figure 10:
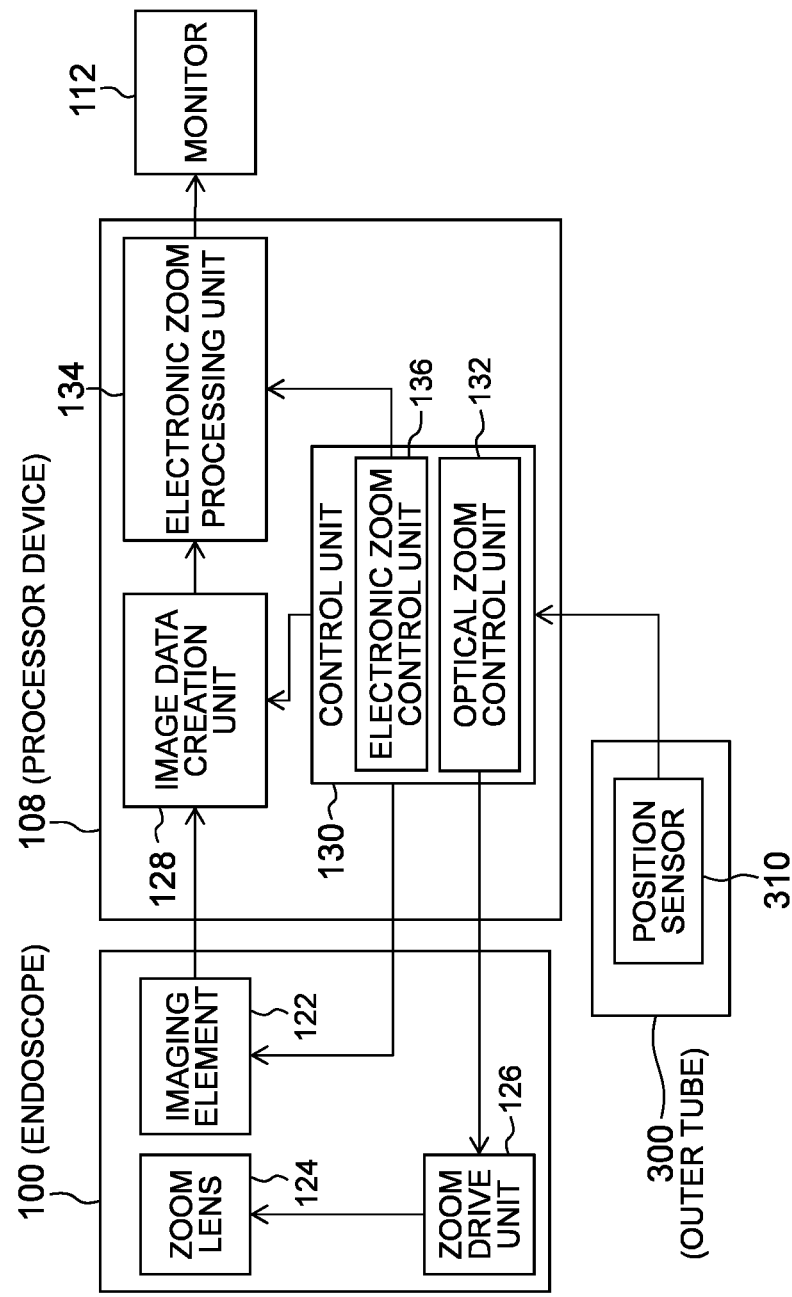
FIG. 10 is a functional block diagram showing a configuration of a main part of an endoscopic surgery device in accordance with a fourth embodiment.

FIG. 10 is a functional block diagram showing a configuration of a main part of an endoscopic surgery device in accordance with the fourth embodiment. In FIG. 10, a component that is identical with or corresponds to that of Figures shown above is designated by the same reference numeral as that of the Figures.

The fourth embodiment is an aspect of a combination of the second embodiment and the third embodiment. That is, as shown in FIG. 10, the control unit 130 of the processor device 108 includes the optical zoom control unit 132 and the electronic zoom control unit 136. The optical zoom control unit 132 controls movement of the zoom lens 124 through the zoom drive unit 126 on the basis of a detection result of the position sensor 310. The electronic zoom control unit 136 controls the variable magnification processing by the electronic zoom processing unit 134 on the basis of a detection result of the position sensor 310.

According to the fourth embodiment, since the control unit 130 of the processor device 108 includes the optical zoom control unit 132 and the electronic zoom control unit 136, control in optical zoom can be performed on a priority basis in a case where the endoscope 100 includes the zoom lens 124. On the other hand, in a case where the endoscope 100 includes no zoom lens 124, control in electronic zoom can be performed. Thus, regardless of types of the endoscope 100 (with or without the zoom lens 124), a range of an observation image displayed in the monitor 112 can be continuously changed so as to follow the back-and-forth movement of the treatment tool insertion part 202 with an allowance with respect to the back-and-forth movement of the treatment tool insertion part 202. Thus, the same effect as that of the first embodiment can be obtained.

Here, it is preferable to control the drive of the zoom lens 124 or the variable magnification processing by the electronic zoom processing unit 134 so that a range of an observation image displayed in the monitor 112 is always constant even if the treatment tool insertion part 202 is moved back and forth.

Fifth Embodiment

Next, a fifth embodiment of the present invention will be described. Hereinafter, description of a portion common to the first to fourth embodiments is omitted, and the present embodiment will be described with a focus on characteristics thereof.

Figure 11:
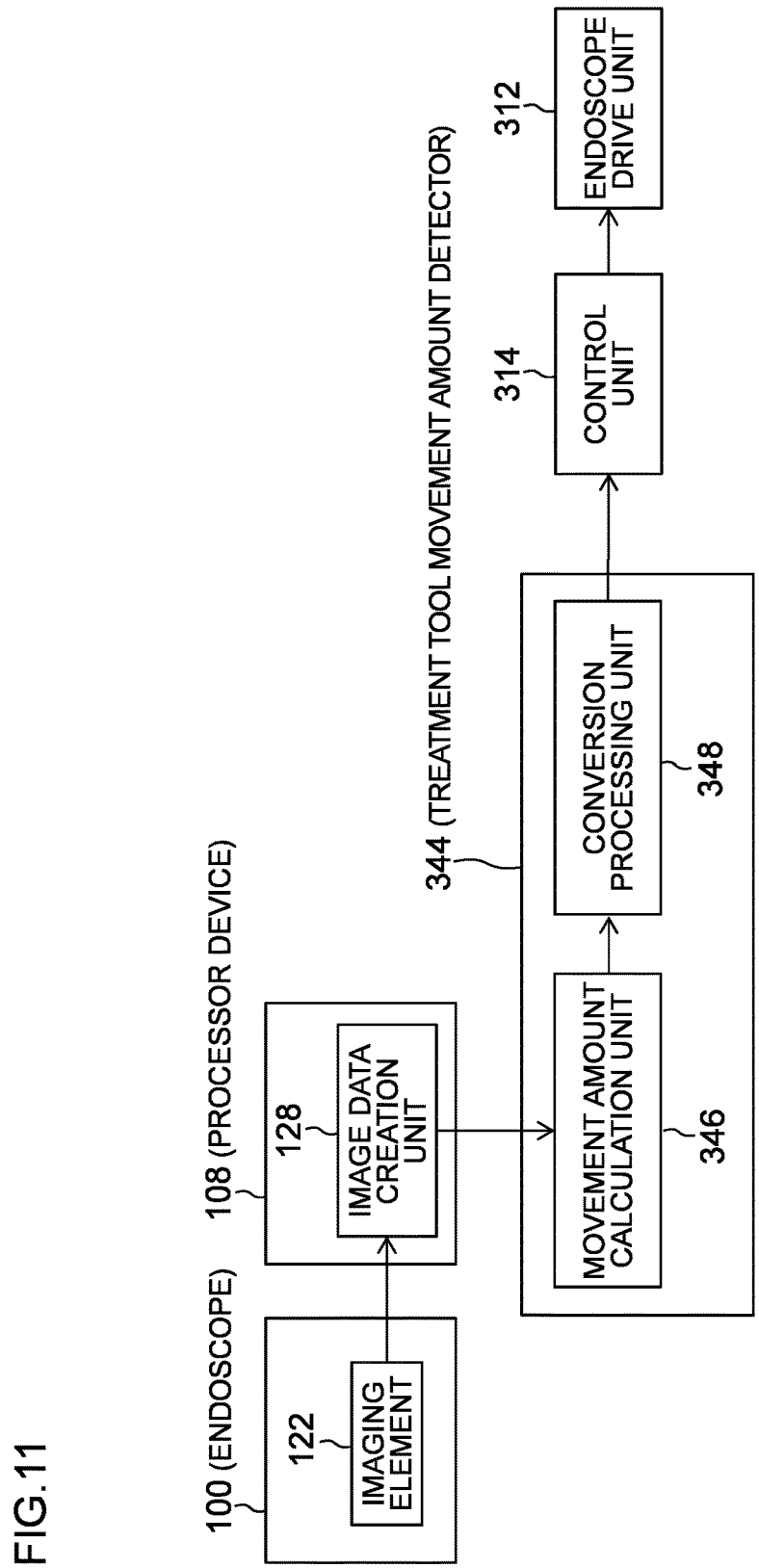
FIG. 11 is a functional block diagram showing a configuration of a main part of an endoscopic surgery device in accordance with a fifth embodiment.

FIG. 11 is a functional block diagram showing a configuration of a main part of an endoscopic surgery device in accordance with the fifth embodiment. In FIG. 11, a component that is identical with or corresponds to that of Figures shown above is designated by the same reference numeral as that of the Figures.

The fifth embodiment includes the treatment tool movement amount detector 344 as detection means that detects the movement amount of the treatment tool insertion part 202 on the basis of image data created by the image data creation unit 128. The treatment tool movement amount detector 344, as with the control unit 314, may be built in the outer tube body 302, or may be connected to the outside of the outer tube body 302 through wiring.

The treatment tool movement amount detector 344 includes a movement amount calculation unit 346 (calculation means), and a conversion processing unit 348 (conversion means).

Figure 12:
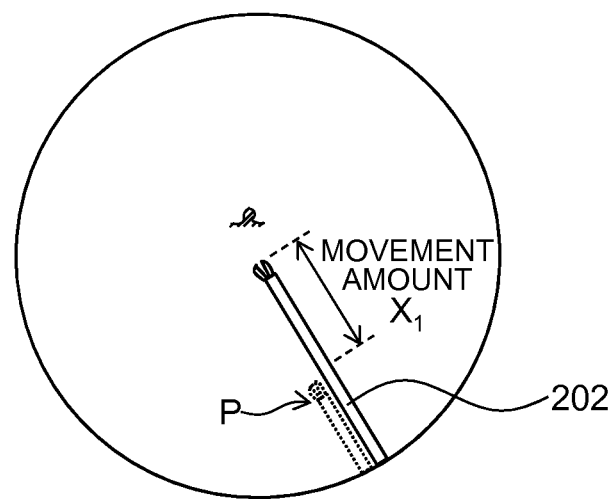
FIG. 12 is an illustration for describing a difference between a movement amount in an endoscope image and an actual movement amount.
Figure 12:
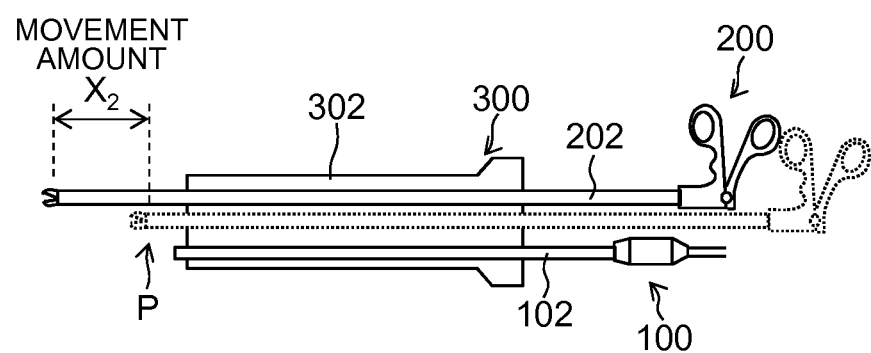

The movement amount calculation unit 346 calculates the movement amount of the treatment tool insertion part 202 on the basis of image data created by the image data creation unit 128. The movement amount calculated at this time is a movement amount $X_1$ in an observation image as shown in portion (A) of FIG. 12, and is different from an actual movement amount $X_2$ shown in portion (B) of FIG. 12. Here, a reference character P designates a starting position of movement of the treatment tool insertion part 202.

The conversion processing unit 348 converts the movement amount $X_1$ in the observation image calculated by the movement amount calculation unit 346 into the actual movement amount $X_2$. Specifically, the movement amount $X_1$ in the observation image is converted into the actual movement amount $X_2$ with reference to a look-up table. Here, a correspondence relationship between the movement amount $X_1$ in the observation image and the actual movement amount $X_2$ is uniquely determined from a clearance (distance) between the treatment tool insertion part 202 and the endoscope insertion part 102, a field angle of the imaging element 122, or the like, and data showing the correspondence relationship is stored in a memory (not shown) as the look-up table.

The movement amount $X_2$ of the treatment tool insertion part 202 acquired by the conversion processing unit 348 is outputted to the control unit 314 as a detection result of the treatment tool movement amount detector 344.

The control unit 314 controls the back-and-forth movement of the endoscope insertion part 102 through the endoscope drive unit 312 on the basis of the detection result of the treatment tool movement amount detector 344. That is, the control unit 314 does not allow the endoscope insertion part 102 to move back and forth if the movement amount $X_2$ of the treatment tool insertion part 202 is within the allowance range, and allows the endoscope insertion part 102 to move back and forth if the movement amount $X_2$ of the treatment tool insertion part 202 is not within the allowance range.

According to the fifth embodiment, an actual movement amount at the time when the treatment tool insertion part 202 is moved back and forth, is detected on the basis of an image data. Thus, it is possible to move the endoscope insertion part 102 back and forth, with an allowance with respect to the back-and-forth movement of the treatment tool insertion part 202, and the same effect as that of the first embodiment can be obtained.

Here, a range of an observation image displayed in the monitor 112 may be changed by optical zoom or electronic zoom, instead of by a back and forth movement of the endoscope insertion part 102, as with the second to fourth embodiments described above.

Sixth Embodiment

Next, a sixth embodiment of the present invention will be described. Hereinafter, description of a portion common to the first to fifth embodiments is omitted, and the present embodiment will be described with a focus on characteristics thereof.

Figure 13:
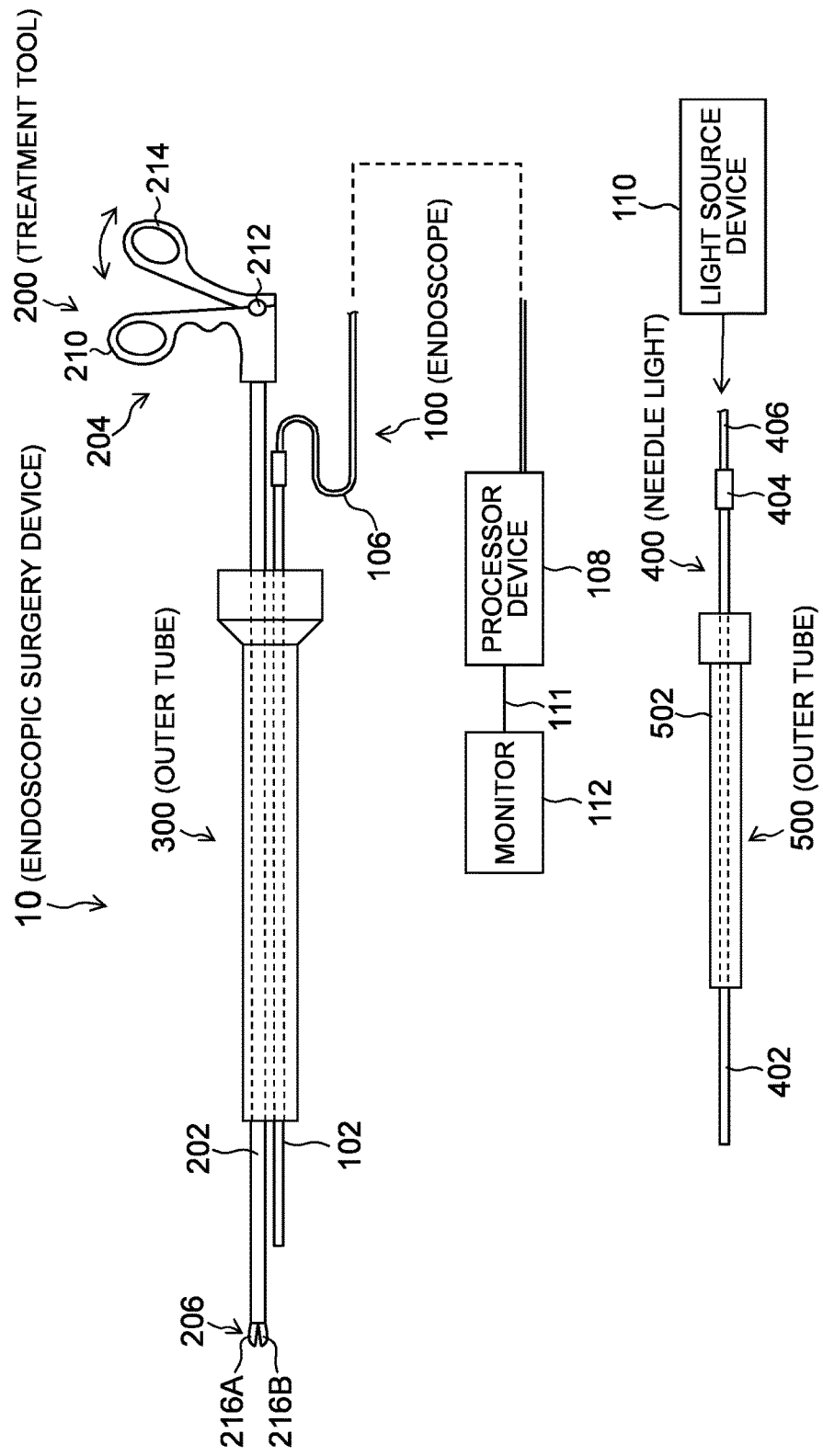
FIG. 13 is a schematic configuration diagram showing an endoscopic surgery device in accordance with a sixth embodiment.

FIG. 13 is a schematic configuration diagram showing an endoscopic surgery device in accordance with the sixth embodiment. In FIG. 13, a component that is identical with or corresponds to that of Figures shown above is designated by the same reference numeral as that of the Figures.

The sixth embodiment is different from the embodiments described above in that the endoscope 100 includes no illumination means for illuminating the inside of a body cavity. Thus, as shown in FIG. 13, the sixth embodiment includes a needle light 400 as a lighting for illuminating the inside of a body cavity, and an outer tube 500 for guiding the needle light 400 into the body cavity.

The needle light 400 includes an elongated insertion part 402 that is to be inserted into a body cavity of a patient, a connection part 404 provided on a proximal end side of the insertion part 402, and a light cable 406 extending from a back end (proximal end side) of the connection part 404. The light cable 406 is provided at its end with a connector (not shown), and the connector is detachably connected to the light source device 110.

The insertion part 402 is provided in its distal end surface with an illumination window (not shown), and behind the illumination window, an emission end of a light guide (not shown) is arranged. The light guide is inserted into the insertion part 402, the connection part 404, and the light cable 406, and an incident end of the light cable 406 is arranged in a connector (not shown). Thus, when the connector is connected to the light source device 110, an illumination light from the light source device 110 is guided to the distal end side of the insertion part 402 through the light guide and emitted into a body cavity through the illumination window.

The outer tube 500 includes an outer tube body 502 that is a guide member to be penetrated through a body wall of a patient and inserted into the body cavity. Inside the outer tube body 502, there is provided an insertion path (not shown) formed so as to penetrate along an axial direction of the outer tube body 502. The insertion path is configured so that the insertion part 402 of the needle light 400 can be inserted (insertable) thereinto and movable back and forth.

Figure 14:
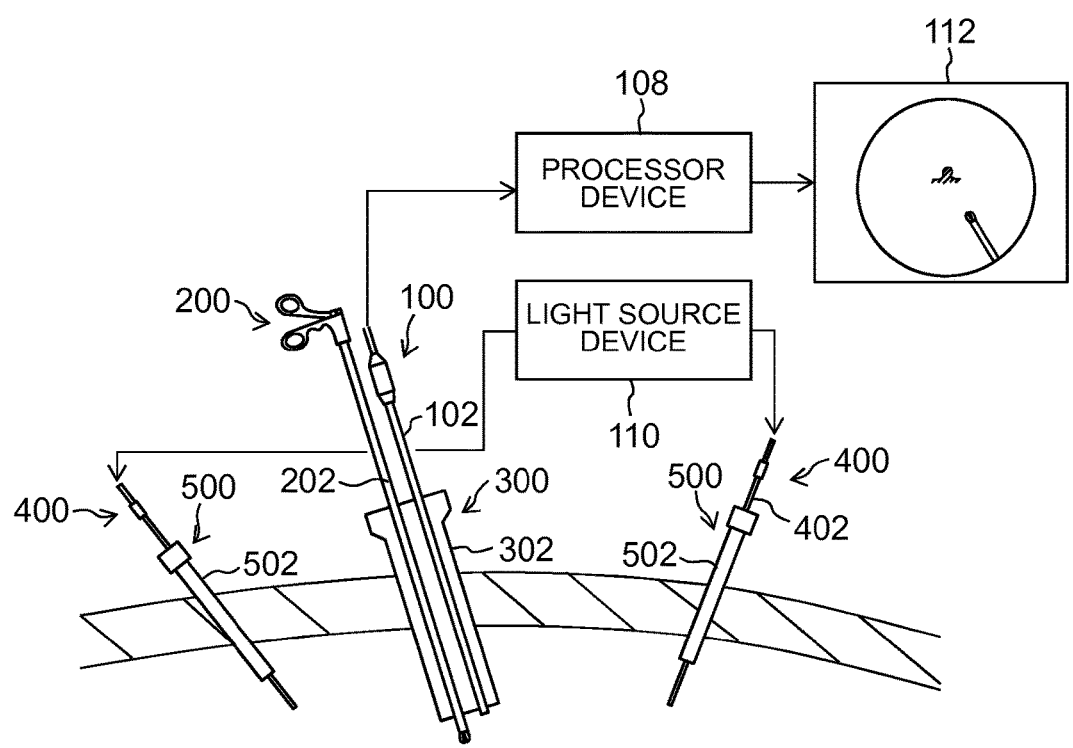
FIG. 14 is an explanation diagram showing a state where an endoscopic surgery device in accordance with the sixth embodiment is used.

FIG. 14 is an explanation diagram showing a state where an endoscopic surgery device according to the sixth embodiment is used. In FIG. 14, a component that is identical with or corresponds to that of Figures shown above is designated by the same reference numeral as that of the Figures.

In the sixth embodiment, since the endoscope 100 includes no illumination means for illuminating the inside of a body cavity, one or more needle lights 400 are used in a case where an operation is performed by using the endoscope 100 and the treatment tool 200 which are guided into the body cavity through the outer tube 300, as shown in FIG. 14. FIG. 14 shows a case where two needle lights 400 and 400 are used.

The needle lights 400 are guided into the body cavity in a state where the needle rights are inserted into an insertion path (not shown) of the outer tube bodies 502 that penetrate a body wall. Then, illumination light from the light source device 110 is supplied to each of the needle lights 400, and the illumination light is emitted into the body cavity through an illumination window (not shown) provided in a distal end surface of the needle light 400.

According to the sixth embodiment, desired brightness can be secured in a body cavity with the illumination lights emitted from the needle lights 400 even if the endoscope 100 does not include illumination means for illuminating the inside of the body cavity. Accordingly, it is possible to observe a state in the body cavity with the monitor 112.

In addition, since the endoscope 100 does not include illumination means for illuminating the inside of the body cavity, an occupied space for arranging an illumination window and a light guide, which are provided in a conventional endoscope, becomes unnecessary. As a result, an outer diameter of the endoscope insertion part 102 can be reduced, and thus an outer diameter of the outer tube 300 also can be reduced. Therefore, since an opening size of an opening (insertion hole) formed in a body wall can be reduced, it is possible to make a postoperative scar inconspicuous to enable a burden to a testee to be reduced.

In the present embodiment, although there is explained about a case of application to an endoscope without illumination means. However, the present embodiment is not limited to this case. The present embodiment can be applied to an endoscope including auxiliary illumination means capable of emitting auxiliary illumination light, for example. If an endoscope includes the auxiliary illumination means, it is possible to reduce a diameter of the endoscope as compared with a conventional general endoscope, and the same effect as that of the present embodiment can be obtained.

In addition, in the present embodiment, although there is described a case where the needle lights 400 are inserted into a body cavity through the outer tube 500, for an example, there may be an aspect in which needle lights 400 are inserted into a body cavity of a patient without using the outer tube 500.

As above, although the endoscopic surgery device according to the present invention has been described in detail, the present invention is not limited to the examples above, and may include various modifications and variations within a range without departing from the essence of the present invention as a matter of course.

What is claimed is:
1. An endoscopic surgery device comprising:
    a guide member configured to penetrate through a body wall to be inserted into a body cavity;
    an endoscope insertion path which is provided inside the guide member, and into which an endoscope configured to observe an inside of the body cavity is inserted in a back-and-forth movable manner;
    a treatment tool insertion path which is provided inside the guide member, and into which a treatment tool configured to inspect or treat a diseased part in the body cavity is inserted in a back-and-forth movable manner;
    a position sensor configured to detect a movement amount of the treatment tool with respect to the guide member when the treatment tool inserted into the treatment tool insertion path moves back and forth; and
    an image capture controller, wherein a range of an observation image acquired by the endoscope is not changed if the movement amount of the treatment tool is within a predetermined range when the movement amount of the treatment tool is detected by the position sensor, and the range of the observation image is changed in accordance with the movement amount of the treatment tool if the movement amount of the treatment tool is not within the predetermined range,
wherein outside the predetermined range, a ratio of a movement amount of the endoscope to the movement amount of the treatment tool is equal to one.

2. The endoscopic surgery device according to claim 1, wherein the image capture controller changes the range of the observation image in proportion to the movement amount of the treatment tool if the movement amount of the treatment tool is not within the predetermined range.

3. The endoscopic surgery device according to claim 1, wherein the image capture controller is an endoscope movement control unit, wherein the endoscope is not moved back and forth if the movement amount of the treatment tool is within the predetermined range when the movement amount of the treatment tool is detected by the position sensor; and the endoscope is moved back and forth in accordance with the movement amount of the treatment tool if the movement amount of the treatment tool is not within the predetermined range.

4. The endoscopic surgery device according to claim 1, wherein the image capture controller is a zoom control unit, wherein a magnification of the observation image is not changed if the movement amount of the treatment tool is within the predetermined range when the movement amount of the treatment tool is detected by the position sensor; and the magnification of the observation image is changed in accordance with the movement amount of the treatment tool if the movement amount of the treatment tool is not within the predetermined range.

5. The endoscopic surgery device according to claim 4, wherein
the endoscope includes a zoom lens configured to be movable in an optical axis direction, and
the zoom control unit includes an optical zoom control unit configured to change the magnification of the observation image by allowing the zoom lens to move in the optical axis direction, based on a detection result by the position sensor.

6. The endoscopic surgery device according to claim 4, wherein the zoom control unit includes an electronic zoom control unit configured to change the magnification of the observation image acquired by the endoscope by performing electronic variable magnification processing to the observation image based on a detection result by the position sensor.

7. The endoscopic surgery device according to claim 1, wherein
the position sensor includes:
a calculation unit configured to calculate the movement amount of the treatment tool in the observation image; and
a conversion unit configured to convert the movement amount of the treatment tool in the observation image calculated by the calculation unit into an actual movement amount.

8. An endoscopic surgery device comprising:
a guide member configured to penetrate through a body wall to be inserted into a body cavity;
an endoscope insertion path which is provided inside the guide member, and into which an endoscope configured to observe an inside of the body cavity is inserted in a back-and-forth movable manner,
a treatment tool insertion path which is provided inside the guide member, and into which a treatment tool configured to inspect or treat a diseased part in the body cavity is inserted in a back-and-forth movable manner;
a position sensor configured to detect a movement amount of the treatment tool with respect to the guide member when the treatment tool inserted into the treatment tool insertion path moves back and forth; and
an image capture controller, wherein a range of an observation image acquired by the endoscope is not changed if the movement amount of the treatment tool is within a predetermined range when the movement amount of the treatment tool is detected by the position sensor, and the range of the observation image is changed in accordance with the movement amount of the treatment tool if the movement amount of the treatment tool is not within the predetermined range,
wherein outside the predetermined range, a ratio of a movement amount of the endoscope to the movement amount of the treatment tool is equal to one,
wherein a movement direction of the treatment tool is parallel to an axial direction of the endoscope.

* * * * *